United States Patent [19]

Stacey et al.

[11] Patent Number: 4,966,847

[45] Date of Patent: Oct. 30, 1990

[54] **RECOMBINANT DNA CLONES CONTAINING A BROAD HOST RANGE GENE FROM *BRADYRHIZOBIUM JAPONICUM***

[76] Inventors: Gary Stacey, 2304 Sutters Mill La., Knoxville, Tenn. 37923; Anthony J. Nieuwkoop, 390 Mayfair St., Holland, Mich. 49424; Zsofia Banfalvi, u7 18/B, H-6723 Szeged Vajda, Hungary

[21] Appl. No.: 78,339

[22] Filed: Jul. 27, 1987

[51] Int. Cl.⁵ ........................ C12N 15/00; C12N 1/00; C12R 1/41; C07H 15/12

[52] U.S. Cl. .............................. 435/172.3; 435/172.1; 435/252.2; 435/252.3; 435/320; 435/878; 536/27; 935/64

[58] Field of Search ............ 536/27; 435/172.1, 172.3, 435/252.2, 252.3, 320, 878

[56] References Cited

PUBLICATIONS

Stacey et al., 1986, pp. 197-201, In: Molec. Gen. Plant. Microbe Interact., Verma et al., eds., Nijhoff: Dordrecht, The Neth.

Russell et al., 1985, J. Bacteriol., 164(3):1301-1308.

Bachem et al., 1986, Mol. Gen. Genet., 203:42-48.

Bassam et al., 1986, Mol. Gen. Genet., 203:49-57.

Nieuwkoop et al., 1987, J. Bacteriol., 169(6):2631-2638.

Cen et al., 1982, Appl. Environ. Microbiol., 43(1):233-236.

*Primary Examiner*—Charles F. Warren

*Assistant Examiner*—David T. Fox

*Attorney, Agent, or Firm*—Foley & Lardner

[57] ABSTRACT

Recombinant DNA clones according to the invention contain a host range gene of *B. japonicum* which is contained within a 3.3 kb HindIII restriction fragment from the *B. japonicum* chromosome. Mutations to this gene change the ability of the bacteria to nodulate different plants. In one example, a Tn5 insertion to this region caused the strain to lose its ability to nodulate siratro, but nodulation of soybeans was unaffected. This gene may be manipulated to extend or restrict the host range of the strain for agricultural purposes.

4 Claims, 2 Drawing Sheets

RECOMBINANT DNA CLONES CONTAINING A BROAD HOST RANGE GENE FROM *BRADYRHIZOBIUM JAPONICUM*

FIELD OF THE INVENTION

The present invention relates to a gene region of *Bradyrhizobium japonicum* which is involved in the ability of this bacteria to nodulate leguminous plants, recombinant DNA clones containing such a gene, and methods of altering this gene region to extend or restrict the host range of a bacterial strain.

BACKGROUND OF THE INVENTION

Bacteria of the genera Rhizobium and Bradyrhizobium possess the ability to infect plants and establish a nitrogen-fixing symbiosis. This process is termed nodulation and the morphological structure formed on the root in which the bacteria reside is termed a nodule. The formation of a nodule is a developmental process both from the standpoint of the bacteria and the plant. Each step in the process likely involves one or more bacterial and plant genes.

The genes in rhizobia (i.e., bacteria of the genera Rhizobium and Bradyrhizobium) involved in nodule formation and function are sometimes referred to as sym (for symbiotic) genes. The sym genes are further classified into three broad categories: nif, fix, and nod genes. The distinction between these genes is not always clear. For the purposes of this invention, nif genes include those that are responsible for production of the nitrogen-fixing enzyme, nitrogenase (i.e., nif KDH) and all other genes that are analogous to nif genes already identified in *Klebsiella pneumoniae*. The fix genes are those genes necessary for nitrogen fixation but which are not comparable to the nif genes of *K. pneumoniae*. The nod genes are those genes involved in the formation of the nodule.

The ability of a specific Rhizobium or Bradyrhizobium to infect a leguminous host is generally restricted; only particular Rhizobium/Bradyrhizobium species-host species combinations are possible. This specificity of interaction is controlled by both plant and bacterial encoded genes. In general, Bradyrhizobium can nodulate a wider range of hosts than can be modulated by Rhizobium species.

Knowledge of the nodulation genetics of Rhizobium species is relatively well advanced, but the same cannot be said with regard to the taxonomically distinct Bradyrhizobium species. Both groups of bacteria contain one set of genes (nodABCDIJ) that are required for nodulation of all hosts; the so-called "common nodulation genes" due to their ability to functionally complement nodulation defective mutants in other rhizobia species (Long, et al. 1982, *Nature* 298:485; Banfalvi, et al., 1983, *Mol. Gen. Genet.* 203:42; Downie, et al., 1983, *EMBO J.* 2:974; Schofield, et al., 1984, *Plant Mol. Biol.* 3:3; Russell, et al., 1985, *J. Bacteriol.* 164:1301; Lamb, et al., 1986, *Mol. Gen. Genet.* 202:512; Noti, et al., 1985, *Proc. Natl. Acad. Sci. U.S.A.* 82:7379; Marvel, et al., 1985, *Proc. Natl. Acad. Sci. U.S.A.* 82:5841; Scott, K. R., 1986, *Nucl. Acids Res.* 14:2905.) A second set of genes has been identified in Rhizobium species that are necessary for nodulation of a particular host. These genes have been termed host specificity (hsn) genes. For example, hsnABCD=nodEFGH (Horvath, et al., 1986, *Cell* 46:335; Kondorosi, et al., 1984, *Molec. Gen. Genet.* 193:445.)

Rhizobium sp. strain MPIK3030, also referred to as NGR234, is capable of nodulating a wide range of leguminous hosts (Trinick, M. J., 1980, *J. Appl. Bacteriol.* 49:39). The ability of this bacteria to nodulate many hosts is apparently due to the presence of several hsn gene loci (Broughton, et al., 1986, *J. Cell. Biol.* 102:1173.) One such locus, affecting the ability to nodulate siratro (*Macroptilium atropurpureum*) has been cloned from this organism (Bachem, et al., 1986, *Mol. Gen. Genet.* 203:42; Bassam, et al., 1986, *Mol. Gen. Genet.* 203:49.) The foregoing papers by Trinick, Broughton, Bachem and Bassam et al. are each hereby incorporated herein by reference.

The foregoing paper by Russell et al. describes recombinant DNA clones, including a clone pRjUT10, comprising a series of contiguous HindIII fragments having sizes of 3.3, 5.6, 3.9, 1.7, 2.3, 4.5, 4.6 and 4.3 kilobases (kb). The 5.6, 3.9 and 1.7 kb fragments were designated a nod region, but no special significance was attributed to the adjoining 3.3 kb fragment.

According to the present invention, it has been found that cloned siratro hsn genes from Rhizobium sp. MPIK 3030 will hybridize to genomic DNA from *B. japonicum*. *B. japonicum* will nodulate siratro in addition to its preferred host, soybean. This invention relates to the identification and isolation of this broad host range hsn locus from *B. japonicum*. This gene is wholly contained in the 3.3 HindIII fragment obtained by Russell et al.

SUMMARY OF THE INVENTION

The present invention identifies a host range gene of *B. japonicum* present in a 3.3 kb HindIII restriction fragment derived from the *B. japonicum* chromosome. This host range gene may be incorporated into a recombinant DNA clone comprising a vector and the 3.3 kb HindIII fragment or a subfragment thereof containing the gene or a desired part of the gene. Such a recombinant DNA clone can be used to effectively transfer the gene to other bacterial strains.

According to a further aspect of the invention, the host range gene of rhizobia (Bradyrhizobium or Rhizobium) may be altered to extend or restrict the host range of a bacterial strain.

DETAILED DESCRIPTION

The terminology of this invention is briefly described as follows. '*Bradyrhizobium japonicum*" refers to a strain of Gram negative, soil bacteria which can nodulate soybean and a few other leguminous species, and fix nitrogen. A "recombinant DNA clone" is a genetic element (DNA polymer) which is capable of independent replication in bacteria. The clone is composed of a vector, containing the genetic determinants of replication and for selection (e.g., antibiotic resistance), and the insert DNA which is the DNA of interest, i.e. contains one or more genes. In the literature the term "recombinant DNA clone" is also used to describe bacteria containing the foregoing genetic element. This definition is not intended for purposes of the present specification. A "restriction enzyme" is an enzyme capable of cutting double-stranded DNA at a specific site determined by the DNA sequence. Two common restriction enzymes used in experiments with DNA from Rhizobium and Bradyrhizobium bacteria are EcoRI and HindIII. A "restriction enzyme DNA fragment" is a piece of DNA separated from the parent strand by digestion with a restriction enzyme. All of these terms are well known in the art.

The present invention relates to the identification and isolation of a broad host range hsn locus from *Bradyrhizobium japonicum.* The ability of *B. japonicum* to establish a $N_2$-fixing symbiosis with leguminous plants is of great agricultural significance, especially with regard to the primary host plant, soybean, which is the second largest crop plant in the United States. Soybean is also the largest leguminous crop worldwide. The great agronomic importance of symbiotic $N_2$ fixation in soybeans has spurred efforts to genetically improve the symbiosis.

The hsn genes identified in this invention may be manipulated to eliminate nodulation of certain host species or, in opposite fashion, extend the host range of rhizobia to other plant species. The former manipulation is useful for purposes of environmental safety. The ability to limit the host range to only the desired host species provides a margin of safety in introducing genetically improved rhizobia into the environment. On the other hand, it may be desirable to extend the host range of a strain having superior nodulation ability so that such a strain can be used with other leguminous crops.

Figure 1:
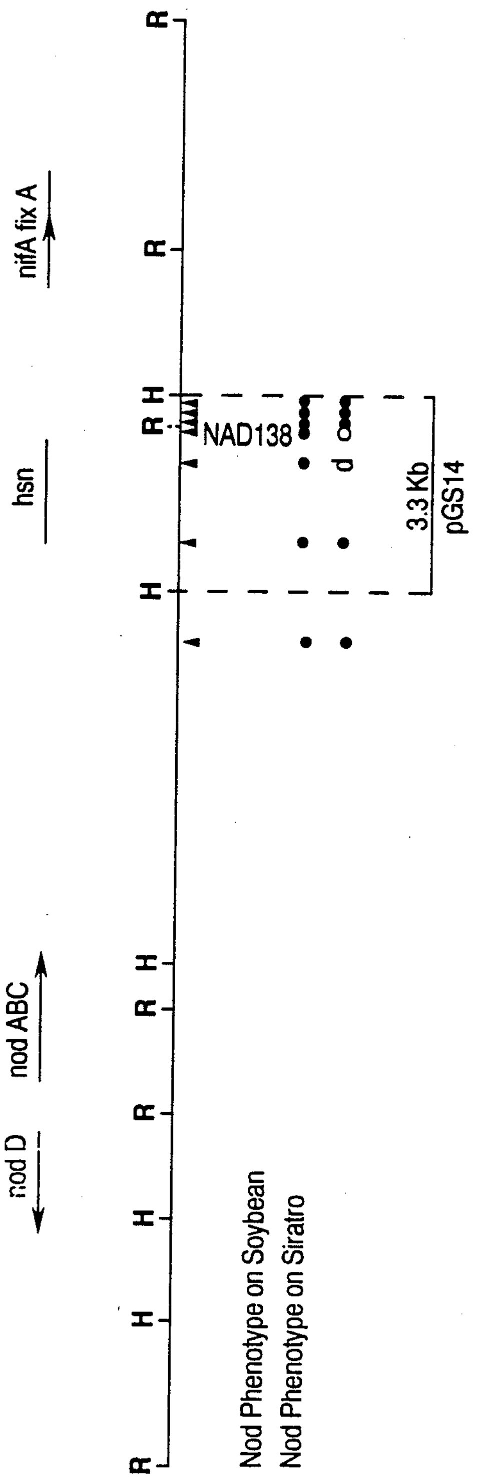
FIG. 1 is a diagram showing nodulation characteristics of *B. japonicum* Tn5 insertion mutants mapping within pRjUT10. The fragment cloned in pGS14 is indicated. The sites of insertions are indicated by triangles, the different symbols underneath correspond to the nodulation phenotype on siratro or soybean, as indicated. Wild type+ (positive): dark circles, Negative-: open circles, delayed nodulation: d; R=EcoRI, H=HindIII restriction sites.

FIG. 1 illustrates the position of the hsn gene on the *B. japonicum* chromosome. The position of this gene and the other regions identified in FIG. 1 are uniquely characterized by the restriction map of the chromosome at the involved region. The restriction map in this instance includes restriction sites for the enzymes EcoRI and HindIII. The map corresponds to the fragment sizes determined by Russell et al. for pRjUT10. The HindIII restriction map sequence is 3.3, 5.6, 3.9, 1.7, 2.3, 4.5, 4.6 and 4.3 kb, the first four of these fragments being indicated from right to left in FIG. 1. The EcoRI sequence shown in FIG. 1 is, from right to left, 3.8, 2.9, 9.4, 1.6 and 7.7 kb.

The example below provides a recombinant DNA clone which contains a gene essential to the ability of *B. japonicum* to nodulate siratro. This cloned region is not essential for nodulation of soybean. The specific recombinant DNA clone referred to herein is pGS14, which contains the 3.3 Kb HindIII restriction fragment from the foregoing sequence. This cloned fragment exhibits DNA-DNA homology to the previously cloned siratro hsn locus from Rhizobium sp. MPIK3030 (Bachem et al., 1986, *Mol. Gen. Genet.* 203:42). A mutation in this region on the *B. japonicum* chromosome results in an inability to nodulate siratro, but the ability to nodulate soybean is retained.

The vector DNA utilized in the above clone could be either plasmid, cosmid, or bacteriophage. The vector DNA could be of a type capable of being introduced and maintained in *B. japonicum.* In the specific clone referred to above, the vector DNA was the plasmid, pAA31P (Ahmed, et al., 1984, Gene 28:37).

The *Bradyrhizobium japonicum* strain from which the 3.3 kb HindIII fragment containing the host range gene can be derived could be any strain containing genes essential for successful nodulation of a leguminous host plant. The specific *B. japonicum* strain used in the example below was strain USDA 110.

The leguminous host used for *B. japonicum* could be varieties of soybean (Glycine max L. Merr.), cowpea (*Vigna unguiculata*), siratro (*Macroptilium atsopurpureum*), or other suitable hosts. The specific hosts used in the example below were soybean, more specifically soybean cultivar Essex, and siratro.

The gene region on pGS14 identified as important to nodulation of siratro is within a 3.3 Kb HindIII restriction enzyme fragment. The identification of this region as essential for nodulation was performed by (1) hybridization with hsn genes from Rhizobium sp. MPIK3030 (Bachem et al., 1986, *Mol. Gen. Genet.* 203:42), and (2) transposon Tn5 mutagenesis which inserts a segment of DNA into the chromosome thereby altering the function of genes adjoining it. FIG. 1 shows the results of a variety of Tn5 inserts at different locations. The open circle corresponding to the NAD138 insert indicates that a Tn5 insert at this location destroyed the strain's ability to nodulate siratro, but that nodulation of soybean was unaffected. The dark circles at other insert locations indicate that inserts at these locations had no effect on nodulation of either soybean or siratro. Thus, the gene, or part thereof affecting nodulation of siratro, is located between the two insert locations on opposite sides of the insert for NAD138.

Clone pGS14 is a subclone of pRjUT10, that is, it contains the 3.3 HindIII fragment also found in pRjUT110, but not the other adjoining HindIII fragments. Clone pGS14 could be further subdivided to provide alternative recombinant DNA clones according to the invention containing the hsn gene using restriction enzymes other than HindIII which restrict the DNA strand at different locations. For example, in FIG. 1, a right end portion of the 3.3 Kb fragment could be removed using EcoRI, which has a restriction site within the 3.3 kb HindIII fragment, to provide a subclone of pGS14.

The identified hsn region can be manipulated to narrow or extend the host range of strains of *B. japonicum* or other Rhizobium/Bradyrhizobium species. More specifically, the hsn gene according to the invention may be transferred to a *B. japonicum* or other strain lacking this gene according to a method of the invention. Using an appropriate recombinant DNA clone containing the hsn region, such as pGS14, the strain lacking this gene may be imparted with the host range of the original strain. The step of transferring the gene may be carried out by conventional genetic transfer techniques, such as triparental mating according to the method of Long et al, *Nature,* 1982, 298:485–488, utilizing plasmids such as pLAFRl and pVK102. The desired strains are then obtained by selective culturing in the presence of an antibiotic to which strains containing the recombinant DNA are resistant. The surviving strains of Rhizobium or Bradyrhizobium have the host range gene according to the invention incorporated therein.

Clone pGS14 is derived from the single chromosome of *B. japonicum* consisting of approximately 7,000 Kb. The basic laboratory techniques used to identify the host range gene from *B. japonicum* strain I-110 and form the corresponding recombinant DNA clone are well known in the art and are not set forth in detail in the example below other than by reference to publications describing the details of the techniques, the contents of which publications are hereby incorporated herein by reference.

The specific hsn gene according to the invention demonstrates substantial homology (approximately 60–70%) towards a corresponding hsn gene in Rhizobium strain MPIK3030. Based on this homology, manipulation of the *B. japonicum* hsn gene by any of the methods described above should be effective to change the host range of any of the species nodulated by MPIK3030, including soybean, siratro, cowpea, and winged bean (*Psophocarpus tetragonolobus.*) The latter is a crop of significant agricultural potential due to its high nutritional value. The method of the present invention could be used, for example, to prepare a species of Rhizobium or Bradyrhizobium specific for nodulating winged bean but not soybean, eliminating any potential problem with cross-over contamination.

The following example outlines the isolation and identification of the hsn locus described and demonstrates its essential role in the nodulation of siratro.

EXAMPLE

General Methods:

Bacterial strains and plasmids used in this example are listed in Table 1. *B. japonicum* cultures were grown in YS medium which containing 1 gram (gm) per liter yeast extract added to the minimal salts/vitamin base of Bishop et al., 1976, *Plant Physiol.* 57:542-546, or in RDY medium containing, per liter, 5 gm gluconic acid, 1 gm glutamic acid, 1 gm yeast extract and mineral salts/vitamin base. *Escherichia coli* cultures were grown in LB medium (Maniatis, et al., 1982, *Molecular Cloning: A Laboratory Manual,* Cold Spring Harbor Laboratory, Cold Spring Harbor, N.Y.). *Rhizobium* sp. strain MPIK3030 was grown in TYA (Orosz, et al., 1973, *Mol. Gen. Genet.* 125:341) or TY (Beringer, 1974, *J. Gen. Microbiol.* 84:188) medium.

TABLE 1

Bacterial Strains and Plasmids

| Bacterial Strain, Plasmid, or Bacteriophage (Source) | Relevant Characteristics |
|---|---|
| Bacteria | |
| *B. japonicum* USDA 110 (1) | Wild type, colony type I110 |
| *E. coli* DH1 (2) | $F^-$, recA1, endA1, gyrA96, thil, $hsdR^{17}$, $sup^{E44}$, $lambda^-$ |
| *E. coli* EG47 (3) | hsdR, lac, gal, $rps^{L594}$ |
| Rhizobium sp. MPIK3030 (4) | wild type |
| Plasmids | |
| pRjUT10 (5) | pHC79 clone of *B. japonicum* |
| pRK2073 (6) | $Trimethoprim^r$, $tra^+$ |
| pCB507 (4) | pLAFR1 derivative carrying the hsn region of R. sp. strain MP1K3030 |
| pGS14 | PAA31P subclone containing a 3.3 kb HindIII fragment of the *B. japonicum* genome |
| Bacteriophages | |
| P1 Tn5 (7) | $Km^r$ |
| P1 In5::lac | $Km^r$ |

Sources:
1. Kuykendall et al, 1976, Appl. Environ. Microbiol. 32:511.
2. Low, 1968, Proc. Natl. Acad. Sci. USA 60:160-166.
3. Goldberg, 1974. J. Bacteriol. 118:810.
4. Bachem et al, 1986, Mol. Gen. Genet. 203:42.
5. Russell et al, 1985, J Bacteriol. 164:1310.
6. Leong et al, 1982, J. Biol. Chem. 257:8724.
7. Quinto et al, 1984, Appl. Environ. Microbiol. 47:436.

DNA Isolation:

Plasmid DNA was isolated on a large scale as described by Davis, et al. 1980, *Advanced Bacterial Genetics,* Cold Spring Harbor Laboratory, Cold Spring Harbor, N.Y. or on a small scale essentially as described by Maniatis et al. cited above.

Southern blotting and hybridization:

DNA restriction fragments were electrophoresed in agarose gels and transferred to nitrocellulose filters as described in Southern, 1975, *J. Mol. Biol.* 98:503. The DNA fragment containing the hsn genes of Rhizobium sp. MPIK3030 was reisolated from agarose gels by the procedure of Maniatis et al., noted above and labeled by the random primer method of Feinberg and Vogelstein, 1982, *Anal. Bichem.* 132:6–13. Hydribizations were carried out in 50% formamide buffer at 37° C. according to Kondorosi et al., 1982, *Mol. Gen. Genet.* 188:433 Filters were washed at 37° C. twice for 1 h in 2× SSC (1×SSC contains 15 mM sodium citrate and 150 mM NaC1 [pH 7.0]) and 0.1% SDS and twice for 1 h in 2× SSC. Exposure of x-ray film was as described by Maniatis et al., cited above.

Enzymes and isotopes:

DNA restriction endonucleases and modifying enzymes were purchased from New England Biolabs, Boehringer Mannheim or Bethesda Research Laboratories and were used according to the manufacturers recommendations. Radioactive nucleotides were purchased from New England Nuclear.

Site directed Tn5 mutagenesis:

Tn5 mutagenesis was performed in *E. coli* strain HMS174 according to de Bruijn and Lupski, 1984, Gene 27 131, or in *E. coli* strain EG47 according to Quinto and Bender, 1984, *Appl. Environ. Microbiol.* 47:436. Mutated fragments were conjugated from *E. coli* to *B. japonicum* USDA 110 by the triparental mating system described by Ditta et al., 1980, *Proc. Natl. Acad. Sci.* U.S.A. 77:7347. The Tn5 mutated fragments were marker exchanged for the corresponding wild-type DNA by the double reciprocal crossover technique of Ruvkin and Ausubel, 1981, *Nature* 289:85. The occurrence of the reciprocal recombination event was confirmed by hybridizing EcoRI digests of total DNA isolated from the mutants with a Tn5 probe, pSup 1011 (Simon, et al., 1983, *Biotechnol.* 1:784.)

Plant tests:

Seeds (Glycine max cv. Essex) were surface sterilized and germinated as described in Wacek and Brill, 1976, *Crop Sci.* 15:519. Seedlings (2 days old) were planted in 35 ml serum vials containing sterile vermiculite saturated with sterile plant nutrient solution (PNS) supplemented with 1% sucrose and covered with sterile 18 oz. Whilpak bags (Nasco). Plants were maintained for 21 days at 26° C. in a growth room supplying 320 $Em^{-2}S^{-1}$ with a 14 hour photoperiod. Nitrogen fixation was detected by the acetylene reduction assay using a Shimadzu GC-8A gas chromatograph equipped with a 6 feet Poropak R column. The detector was maintained at a temperature of 100° C. and the column at 75° C. Plant roots were visually examined for nodules. For delayed nodulation assays, seedlings were sprouted as before, then grown three to a pack in clear plastic pouches (Dispo Seed Pack, Northrup King Seed Co.) as described in Halverson et al., 1985, *Plant Physiol.* 77:621. Siratro (*Macroptilium atropurpureum*) plant assays was carried out in test-tubes on nitrogen-free medium as described in Kondorosi, et al., 1977, *Mol. Gen. Genet.* 151:221.

Results:

The nodABCD genes of *R. meliloti* were cloned by Long et al., 1982, *Nature* (London) 298:485, and located on a 8.5 Kb EcoRI fragment. This 8.5 Kb fragment was used as a hybridization probe to a genomic library of *B. japonicum* USDA 110. A single clone (pRjUTlO) was obtained that showed homology to the *R. meliloti* nod gene fragment (Russell et al., 1985, cited above). The 7.5 Kb EcoRI fragment isolated from plasmid pCB507 (Bachem et al., 1986, cited above) was then hybridized to pRjUTlO. This 7.5 kb EcoRI fragment encodes the ability for Rhizobium sp. MPIK3030 to nodulate siratro. The hybridization results indicated that a single 3.3 Kb HindIII fragment contained within pRjUT10 showed homology to the siratro hsn genes. This region is designated hsn in FIG. 1.

Figure 2:
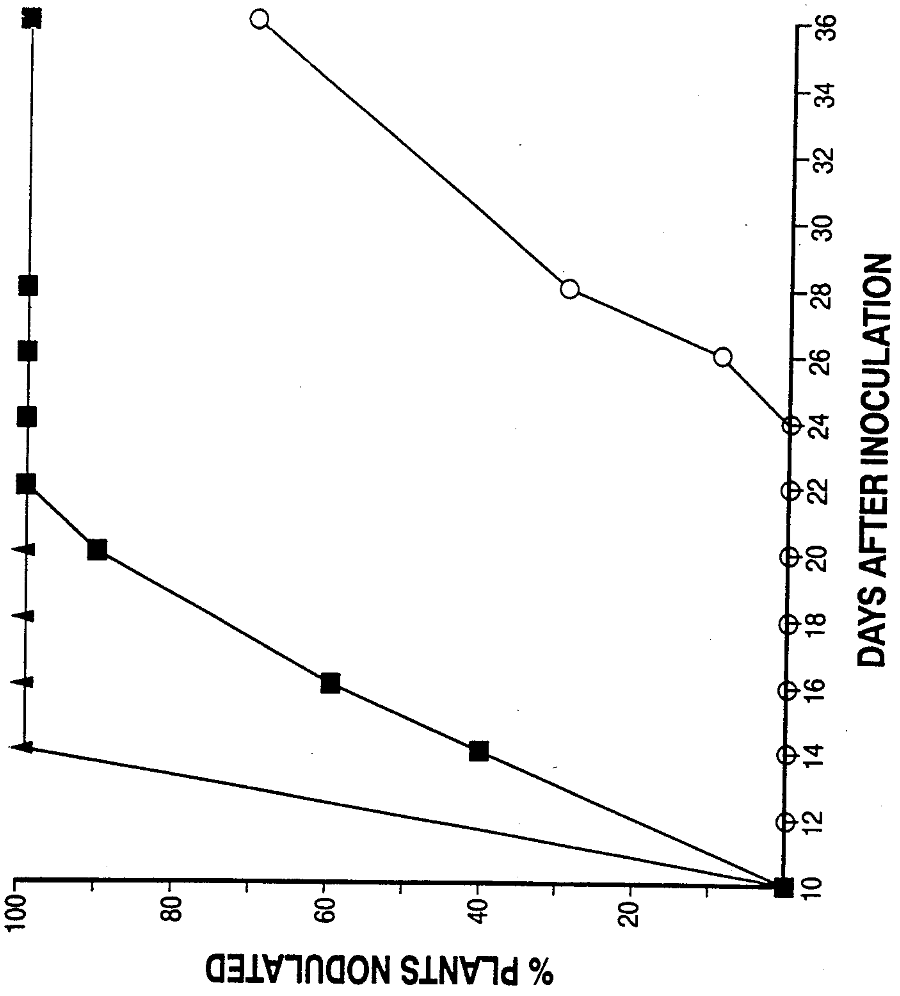
FIG. 2 is a diagram showing nodulation kinetics of siratro plants inoculated with Rhizobium sp. MPIK3030 (dark triangles), *B. japonicum* USDA 110 (dark boxes), and *B. japonicum* mutant NAD138 (open circles). Nodulation kinetics are shown as percent of plants nodulated from 15 total plants.

Since *B. japonicum* nodulates siratro, the possibility existed that the identified region contained genes essential for nodulation of this alternate host. To test this, Tn5 was inserted into this region and the nodulation phenotype tested on soybean and siratro. On soybean, the mutant (NAD138) produced nodules with little or no delay. However, when tested on siratro, this mutant could not elicit nodules until after 20 days. The results of these plant tests are set forth graphically in FIG. 2.

A second mutation in the region, generated by Tn5-lac mutagenesis (Kroos, et al., 1984, *Proc. Natl. Acad. Sci. U.S.A.* 81:5816) was located 0.6 Kb left of NAD138 and was found to have an altered nodulation phenotype on siratro. Nodulation of siratro was delayed 3–4 days by an insertion at this location. However, Tn5 insertions located to the right of NAD138 within the 0.5 Kb EcoRI-HindIII fragment and about 2 Kb to the left of that EcoRI site showed a wild type nodulation pattern on siratro, i.e. had no effect of delaying or preventing siratro nodulation using the strain. Thus, the siratro hsn specific region can be localized to the rightmost end of the large 9.4 Kb EcoRI fragment of pRjUTlO and wholly contained within the 3.3 Kb HindIII fragment.

This 3.3 Kb HindIII fragment was isolated from restricted pRjUTlO and subcloned into the vector pAA31P (Ahmed, A., et al., 1984, Gene 28:37). The resulting plasmid was named pGS14.

It will be understood that the above description is of preferred exemplary embodiments of the invention, and that the invention is not limited to the specific forms shown. Modifications may be made in the compositions and methods according to the invention without departing from the scope of the invention as described in the appended claims.

What is claimed is:

1. A recombinant DNA clone consisting essentially of a vector and a gene encoding the siratro hsn specific functions of *B. japonicum,* said gene being one located between nodABCD genes and nifA, fixA genes on the chromosome of *B. japonicum,* wherein said host range gene is contained in a 3.3 Kb HindIII restriction fragment in a region of having a HindIII restriction map sequence of 3.3, 5.6, 3.9, 1.7, 2.3, 4.5, 4.6 and 4.3 kb as consecutive, contiguous fragments of DNA in a strain of *B. japonicum* characterized by such a restriction map sequence.

2. A method for restricting the host range of a bacterial strain of *B. japonicum,* which strain nodulates both soybean and siratro, which method comprises disrupting a host range gene of said strain, which host range gene is located between nodABCD genes and nifA and fixA genes on the chromosome of *B. japonicum* and is contained in a 3.3 Kb HindIII restriction fragment in a region of having a HindIII restriction map sequence of 3.3, 5.6, 3.9, 1.7, 2.3, 4.5, 4.6 and 4.3 kb as consecutive, contiguous fragments of DNA in *B. japonicum* strains characterized by such a restriction map sequence, so that the resulting strain is unable to nodulate siratro.

3. The method of claim 2, wherein said disrupting step comprises inserting DNA into said gene.

4. A bacterial strain made by the method of claim 2.

* * * * *